United States Patent
Smith

(10) Patent No.: US 8,172,806 B2
(45) Date of Patent: May 8, 2012

(54) SURGICAL PORTAL WITH SEAL SYSTEM

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/764,639

(22) Filed: Apr. 21, 2010

(65) Prior Publication Data

US 2010/0256567 A1  Oct. 7, 2010

Related U.S. Application Data

(62) Division of application No. 11/406,992, filed on Apr. 19, 2006, now Pat. No. 7,717,878.

(60) Provisional application No. 60/674,652, filed on Apr. 25, 2005.

(51) Int. Cl.
*A61M 5/178* (2006.01)

(52) U.S. Cl. .......... 604/167.01; 604/167.03; 604/167.06

(58) Field of Classification Search .................. 604/247, 604/167.01–167.06, 164.01–164.02; 606/108
See application file for complete search history.

(56) References Cited

U.S. PATENT DOCUMENTS

| | | | |
|---|---|---|---|
| 2,836,180 A | 5/1958 | Strauss, Jr. |
| 4,240,411 A | 12/1980 | Hosono |
| 4,473,067 A | 9/1984 | Schiff |
| 4,653,477 A | 3/1987 | Akui et al. |
| 4,715,360 A | 12/1987 | Akui et al. |
| 4,895,346 A | 1/1990 | Steigerwald |
| 4,929,235 A | 5/1990 | Merry et al. |
| 5,080,654 A | 1/1992 | Picha et al. |
| 5,104,379 A | 4/1992 | Nakamura et al. |
| 5,104,383 A | 4/1992 | Shichman |
| 5,122,122 A | 6/1992 | Allgood |
| 5,127,626 A | 7/1992 | Hilal et al. |
| 5,141,498 A | 8/1992 | Chiristian |
| 5,147,305 A | 9/1992 | Nakamura et al. |
| 5,176,651 A | 1/1993 | Allgood et al. |
| 5,209,219 A | 5/1993 | Hollobaugh |

(Continued)

FOREIGN PATENT DOCUMENTS

DE  20307557  10/2003

(Continued)

OTHER PUBLICATIONS

Official Action mailed Apr. 21, 2011 from the Japanese Patent Office in counterpart Japanese Application No. 2006-119907, with English Translation.

*Primary Examiner* — Theodore Stigell

(57) ABSTRACT

A surgical seal system is adapted for use with a cannula assembly having a cannula housing and a cannula sleeve extending from the cannula housing. The surgical seal assembly includes a seal assembly and an adapter assembly. The seal assembly is mountable to the cannula housing. The seal assembly includes a seal housing and a seal defining inner portions adapted to form a substantial seal about an instrument with a first cross-sectional dimension. The adapter assembly includes an adapter body adapted for releasably coupling to the seal housing of the seal assembly. The adapter body has an adapter seal and a tether. The adapter seal is adapted to form a substantial seal about an instrument with a second cross-sectional dimension less than the first cross-sectional dimension. The tether is mountable to the cannula sleeve thus securing the adapter assembly to the cannula.

22 Claims, 13 Drawing Sheets

U.S. PATENT DOCUMENTS

| | | | |
|---|---|---|---|
| 5,221,264 A | 6/1993 | Wilk et al. |
| 5,263,944 A | 11/1993 | Vidal et al. |
| 5,300,036 A | 4/1994 | Mueller et al. |
| 5,312,362 A | 5/1994 | Pfolsgraf et al. |
| 5,338,307 A | 8/1994 | Stephens et al. |
| 5,350,362 A * | 9/1994 | Stouder, Jr. ............. 604/167.03 |
| 5,382,242 A | 1/1995 | Horton et al. |
| 5,385,560 A | 1/1995 | Wulf |
| 5,395,342 A | 3/1995 | Yoon |
| 5,397,335 A | 3/1995 | Gresl et al. |
| 5,437,646 A | 8/1995 | Hunt et al. |
| 5,439,455 A | 8/1995 | Kieturakis et al. |
| 5,460,615 A | 10/1995 | Storz et al. |
| 5,496,280 A | 3/1996 | Wandernbroek et al. |
| 5,512,053 A | 4/1996 | Pearson et al. |
| 5,514,098 A | 5/1996 | Pfoslgraf et al. |
| 5,520,655 A | 5/1996 | Davila et al. |
| 5,531,758 A | 7/1996 | Uschold et al. |
| 5,549,565 A | 8/1996 | Ryan et al. |
| 5,549,594 A | 8/1996 | Brunken |
| 5,569,206 A | 10/1996 | Gorman, Jr. et al. |
| 5,607,397 A | 3/1997 | Stephens et al. |
| 5,693,031 A | 12/1997 | Ryan et al. |
| 5,820,604 A | 10/1998 | Fox et al. |
| 5,820,606 A | 10/1998 | Davis et al. |
| 5,843,040 A | 12/1998 | Exline |
| 5,868,714 A | 2/1999 | Danks |
| 5,871,471 A | 2/1999 | Ryan et al. |
| 6,093,176 A | 7/2000 | Dennis |
| 6,099,505 A | 8/2000 | Ryan et al. |
| 6,123,689 A | 9/2000 | To et al. |
| 6,159,182 A | 12/2000 | Davis et al. |
| 6,165,184 A | 12/2000 | Verdura et al. |
| 6,217,555 B1 | 4/2001 | Hart et al. |
| 6,258,065 B1 | 7/2001 | Dennis et al. |
| 6,572,631 B1 | 6/2003 | McCartney |
| 6,702,787 B2 * | 3/2004 | Racenet et al. ............. 604/256 |
| 2004/0006356 A1 | 1/2004 | Smith |

FOREIGN PATENT DOCUMENTS

| | | |
|---|---|---|
| EP | 0696459 | 2/1996 |
| EP | 0784961 | 7/1997 |
| JP | 2006-205788 | 7/1994 |
| JP | 2007-28561 | 5/1995 |
| WO | 93/19797 | 10/1993 |
| WO | 98/50093 | 11/1998 |

* cited by examiner

SURGICAL PORTAL WITH SEAL SYSTEM

CROSS REFERENCE TO RELATED APPLICATION

This application is a divisional of U.S. application Ser. No. 11/406,992, filed Apr. 19, 2006, now U.S. Pat. No. 7,717,878, which claims priority to and the benefit of U.S. Provisional Application Ser. No. 60/674,652, filed Apr. 25, 2005, the entire contents of which are incorporated herein by reference.

BACKGROUND

1. Technical Field

The present disclosure relates to a surgical portal and, more particularly, relates to a seal system including a seal and an adapter for use with a cannula assembly.

2. Description of the Prior Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. . . . However, despite its recent success and overall acceptance as a preferred surgical technique, minimally invasive surgery, such as laparoscopy, has several disadvantages. In particular, the maintenance of the seal about the surgical instrument within the cannula has proven to be difficult in certain procedures, e.g., in procedures requiring extensive manipulation of the long narrow endoscopic instruments within a remote site. In addition, many conventional seal assemblies are not adapted to accommodate instruments of various sizes, while still maintaining the seal about the inserted instrument. Moreover, many seal assemblies are complex, involving multiple components and accompanying assembly requirements. Despite the availability of trocar assemblies having cannulas of various sizes, there remains a need for apparatus that may be used to vary the size of the aperture within a cannula assembly in a more efficient and efficacious manner.

SUMMARY

A surgical seal system for use with a cannula assembly having a cannula housing and a cannula sleeve extending from the cannula housing is provided. The surgical seal assembly includes a seal assembly mountable to the cannula housing and an adapter assembly adapted for releasably coupling to the seal assembly. The seal assembly includes a seal housing and a seal. The seal defines inner portions adapted to form a substantial seal about an instrument with a first cross-sectional dimension. The adapter assembly includes an adapter body having an adapter seal defining internal portions adapted to form a substantial seal about an instrument with a second cross-sectional dimension different from the first cross-sectional dimension. A tether is connected to the adapter body and is adapted for mounting to the cannula sleeve thus securing the adapter assembly to the cannula. The tether includes a sleeve passageway dimensioned for receiving the cannula sleeve. The tether may include a locking tab and corresponding recess adjacent the sleeve passageway for securing the tether to the cannula sleeve.

The adapter body may include a manual release tab. The release tab is dimensioned for manual engagement by a surgeon to facilitate releasing of the adapter body from the seal assembly. The adapter body includes an entry surface which generally tapers toward a central axis of the adapter body. The tapered surface may be generally frusto-conical in configuration. The adapter body may include an outer wall. The outer wall is adapted for positioning over the seal housing. Preferably, the outer wall of the adapter body is positionable over a peripheral ledge of the seal housing. Preferably, the adapter body comprises an elastomeric material.

The seal assembly includes a seal mount. The seal is molded to the seal mount. The seal mount defines molding apertures to permit flow of seal material therethrough during molding of the seal to the seal mount. Preferably, the seal mount is a generally annular seal mount and wherein the molding apertures are spaced adjacent peripheral areas of the seal mount. The seal assembly may be releasably mountable to the cannula housing.

In another preferred embodiment, an adapter apparatus adapted for releasably coupling to a cannula assembly having a cannula housing and a cannula sleeve is provided. The adapter apparatus includes an adapter body having an adapter seal defining internal portions adapted to form a substantial seal about an instrument and a tether connected to the adapter body and adapted for mounting to the cannula sleeve.

In another preferred embodiment, a surgical seal system for use with a cannula assembly having a cannula housing and a cannula sleeve extending from the cannula housing is provided. The surgical seal assembly includes a seal housing defining a seal axis and having a seal mount at least partially positionable within the cannula housing. The seal mount has a resilient seal member molded thereto. The seal member defines inner portions adapted to form a substantial seal about an instrument. A cover is adapted for mounting to the cannula housing to secure the seal mount within the cannula housing. The cover includes a cover opening for permitting passage of the instrument. The cover may include a plurality of intersecting entry surfaces. The entry surfaces are obliquely arranged relative to the seal axis and are adapted to guide the instrument through the opening of the cover. The seal mount may include a plurality of peripherally disposed apertures whereby anchoring segments of the seal member are received within the apertures to facilitate securing of the seal member to the seal mount.

BRIEF DESCRIPTION OF THE PREFERRED EMBODIMENT(S)

Preferred embodiments of the present disclosure will be readily appreciated by reference to the drawings wherein.

DETAILED DESCRIPTION OF THE PREFERRED EMBODIMENTS

The seal system of the present disclosure provides a substantial seal between a body cavity of a patient and the outside atmosphere during insertion of an object through the apparatus. Moreover, the seal system accommodates objects of varying diameters, e.g., instruments from about 3 mm to about 15 mm, and provides the capability of forming a gas tight seal with each instrument when inserted. This flexibility of the seal system greatly facilitates endoscopic surgery where a variety of instruments having differing diameters are often needed during a single surgical procedure. The seal system of the present disclosure may be adapted for mounting to a conventional cannula assembly or the cannula assembly described hereinbelow.

The seal system may include a first seal assembly which is releasably mountable to the housing of a cannula. The first seal assembly is adapted to form a seal about a first instrument having a first cross-section or diameter. The seal system also may include an adapter assembly which may be connected or attached to the cannula sleeve of the cannula. The adapter assembly is adapted to mount over the seal assembly to form a seal about a second instrument having a second cross-section or diameter different than the first instrument, e.g., a smaller-diameter instrument.

The cannula assembly may be any conventional cannula assembly suitable for the intended purpose of accessing a body cavity to permit introduction of instruments therethrough. The cannula assembly is particularly adapted for use in laparoscopic surgery where the peritoneal cavity is insufflated with a suitable gas, e.g., $CO_2$, to raise the cavity wall from the internal organs therein. The cannula assembly is typically used with an obturator assembly, which is an elongate instrument positionable within the cannula assembly. The obturator assembly may have a sharp end or a blunt end and is utilized to pass through, e.g., abdominal tissue, to facilitate introduction of the cannula assembly within the abdominal cavity. Once access to the abdominal cavity is achieved, the obturator assembly is removed from the cannula assembly to permit subsequent introduction of the surgical instrumentation through the cannula assembly to perform the procedure.

Figure 1:
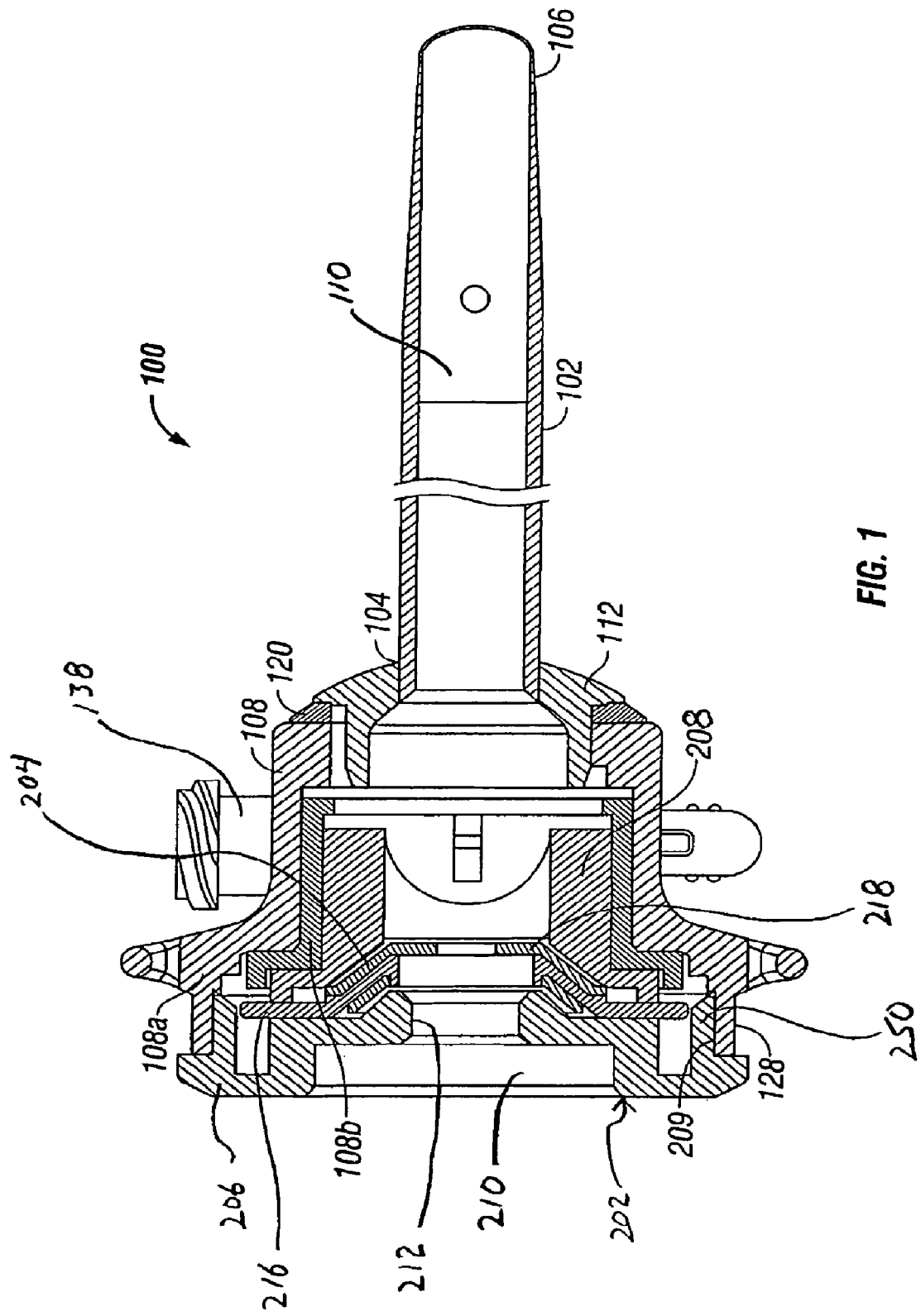
FIG. 1 is a side cross-sectional view of a cannula assembly and seal assembly of the seal system in accordance with the principles of the present disclosure.
Figure 2:
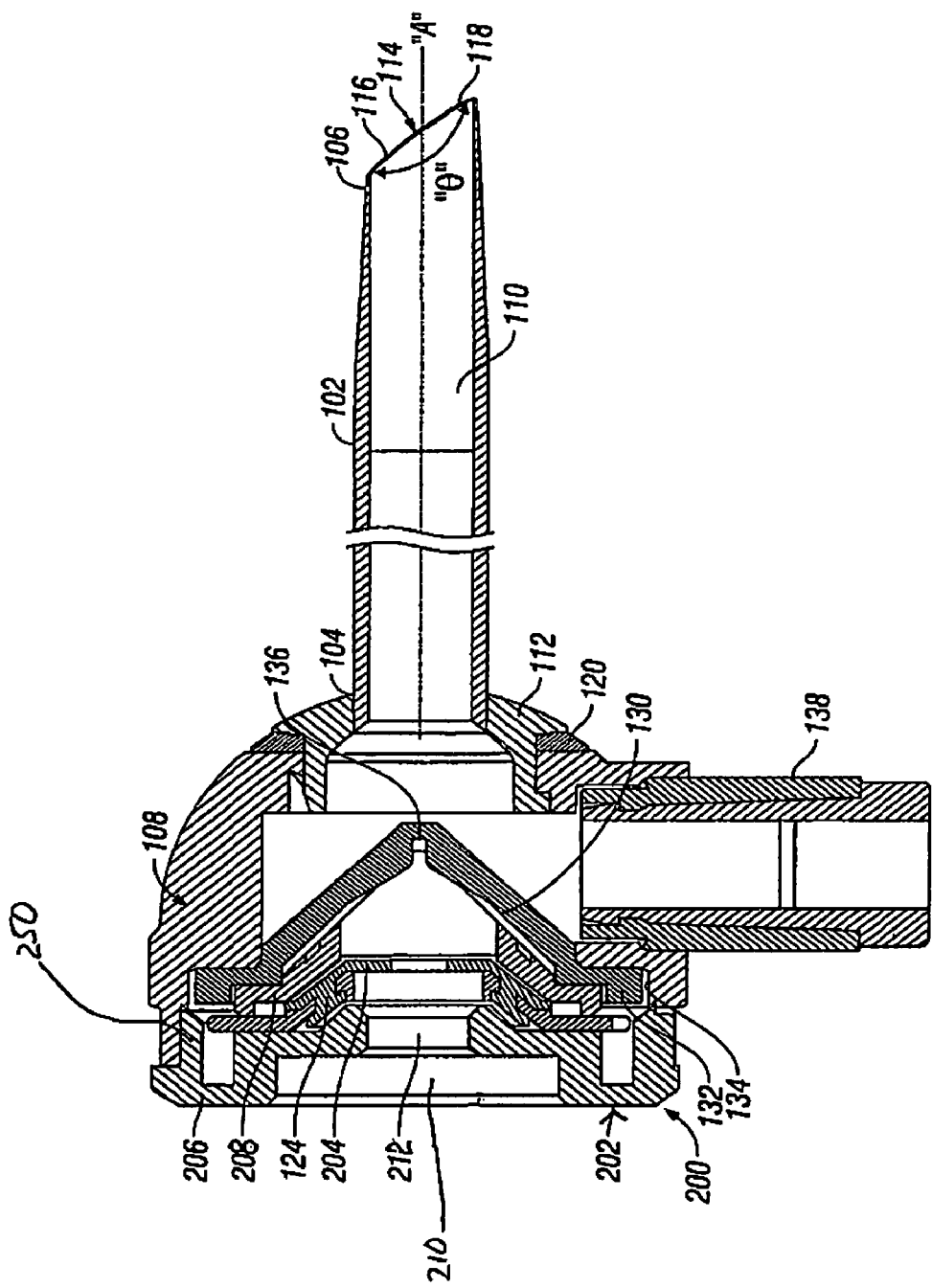
FIG. 2 is a second side cross-sectional view of the cannula assembly and seal assembly.
Figure 3:
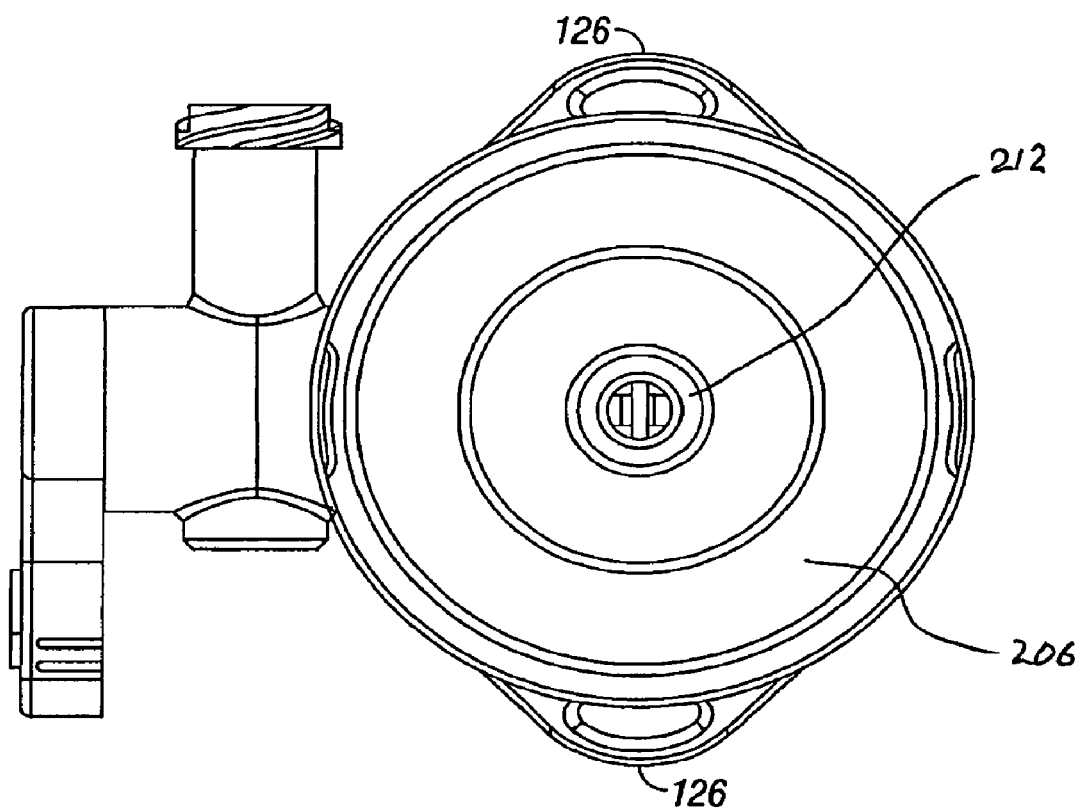
FIG. 3 is a top plan view of the cannula assembly and the seal assembly.

With initial reference to FIGS. 1-3, the preferred cannula assembly 100 includes cannula sleeve 102 having proximal and distal ends 104, 106 and cannula housing 108 mounted to the proximal end 104 of the sleeve 102. Cannula sleeve 102 defines a longitudinal axis "A" extending along the length of sleeve 102. Sleeve 102 further defines an internal longitudinal passage 110 dimensioned to permit passage of surgical instrumentation. Sleeve 102 is a one piece construction and incorporates sleeve flange 112 monolithically-formed at the proximal end 104. Sleeve 102 may be fabricated of stainless steel or another suitable rigid material such as a polymeric material or the like. Sleeve 102 may be clear or opaque. The diameter of sleeve 102 may vary, but, typically ranges from about 3 mm to about 15 mm. The distal end of sleeve 102 preferably defines an oblique surface 114 as shown. The preferred oblique surface incorporates first and second surface 116, 118 intersecting at a slight angle "0", which preferably ranges from about 170° to about 180°.

Cannula housing 108 is connected to sleeve flange 112 of cannula sleeve 102. In one preferred embodiment, the connection is achieved through ultrasonic welding, adhesives, cements, etc. In the alternative, the cannula housing 108 and sleeve flange 112 may be connected through a bayonet, threaded or snap-fit coupling. An O-ring 120 is desirably disposed between an interior bearing surface of cannula housing 108 and an exterior bearing surface of sleeve flange 112 to minimize leakage of gases between the cannula housing 108 and the sleeve flange 112 during use in the laparoscopic procedure.

Cannula housing 108 may include several components, e.g., inner and outer components 108a, 108b connected together to form the cannula housing 108. Cannula housing 108 preferably includes first and second diametrically opposed finger tabs 126. Tabs 126 are dimensioned for grasping by the surgeon. Cannula housing 108 further defines proximal collar 128. Cannula housing 108 may be generally bell-shaped as shown.

Resilient valve 130 is supported within cannula housing 108. Resilient valve 130 includes a circumferential flange 132 which rests on internal ledge 134 within cannula housing 108 such that the resilient valve 130 is supported within cannula housing 108. Valve 130 may be of general duck-bill configuration and defines an interior slit 136 which opens to permit passage of an object and closes in the absence of the object. The valve 130 is desirably a zero closure valve or a slit seal which may be adapted to close when exposed to gaseous pressure of the underlying insufflated cavity, to thereby prevent passage of insufflation gases through cannula assembly 100. In the alternative, valve 130 may be a flat disc-shaped valve, balloon valve, flapper valve, conical valve, etc. . . .

Cannula housing 108 further includes port 138 for connecting a stop cock to the cannula housing 108. The stop cock connects to an external source of insufflation gases for introducing insufflation gases into the body cavity of the patient through cannula sleeve 102. Port 138 is in communication with longitudinal passage 110 of cannula sleeve 102.

Referring now to FIGS. 1-2, seal assembly 200 of the seal system will be discussed in detail. Seal assembly 200 is intended for use with an instrument having a first diameter ranging from about 3 mm to about 7 mm, preferably, about 5 mm. However, seal assembly 200 may be arranged for use with instruments of any size or range of sizes. Seals for trocars typically range from about 3 mm to about 15 mm. Alternatively, seal assembly 200 may also be arranged to form a seal around a surgeon's arm. Seal assembly 200 includes seal housing 202 and seal 204 which is disposed within the seal housing 202. Seal housing 202 may incorporate several housing components connected to each other via any of the conventional means discussed hereinabove or may be a monolithically formed unit. Seal housing 202 defines a central passage extending along the seal axis which is preferably in alignment with axis "A" of cannula sleeve 102 when the seal assembly 200 is mounted to the cannula assembly 100. Seal housing 202 includes cover 206 and seal support 208. Seal 204 is captured between cover 206 and seal support 208. Seal support 208 also assists in retaining zero closure valve 130 at a desired orientation within housing 108.

Figure 4:
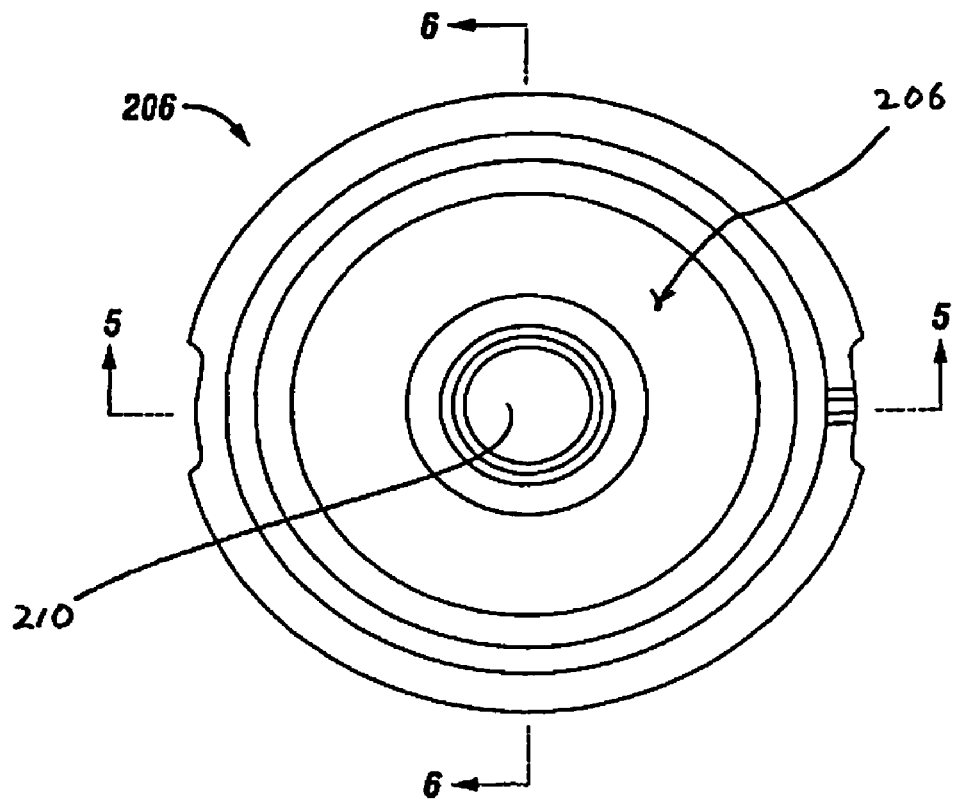
FIG. 4 is a top plan view of the cover of the seal assembly.
Figures 5, 6:
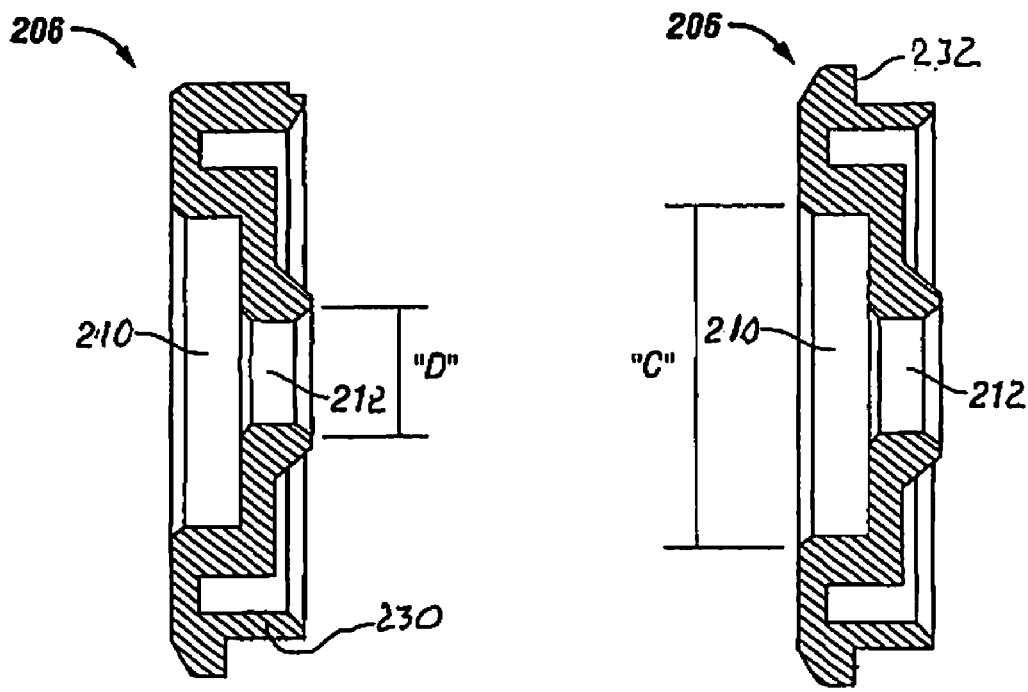
FIGS. 5-6 are cross-sectional views of the cover of the seal assembly respectively taken along lines 5-5 and 6-6 of FIG. 4.

As best depicted in FIGS. 4-6, cover 206 has a stepped configuration defining proximal opening 210 and distal opening 212 distal of the proximal opening 210. Proximal opening 210 is substantially constant in diameter defining a diameter "C" ranging from about 4 mm to about 8 mm. Distal opening 212 defines a diameter "D" ranging from about 2 mm to about 6 mm. Proximal opening 210 and distal opening 212 may be smaller or larger to accommodate smaller or larger size instruments.

Figure 7:
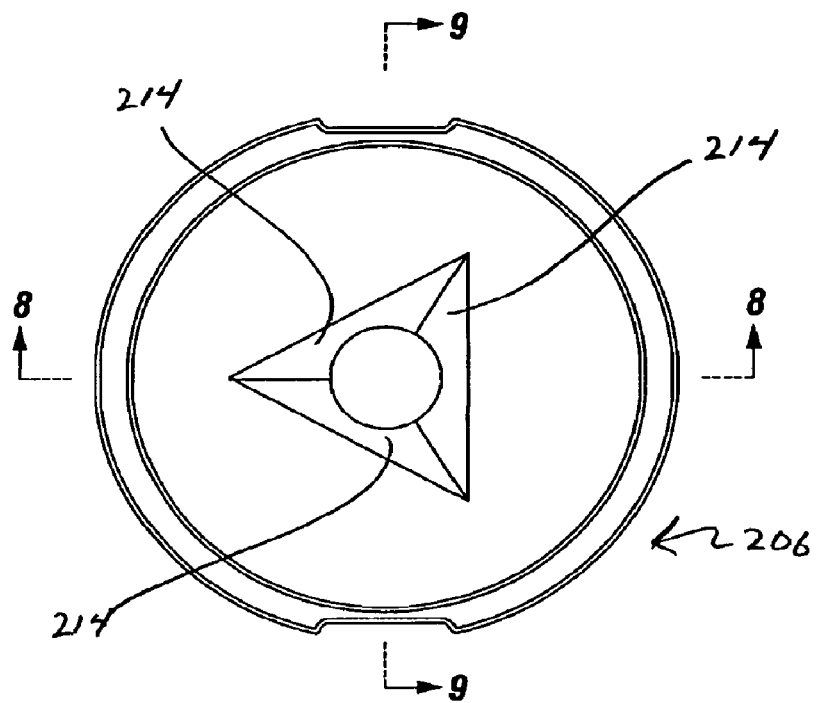
FIG. 7 is a top plan view of an alternate embodiment of the cover of the seal assembly.
Figure 8:
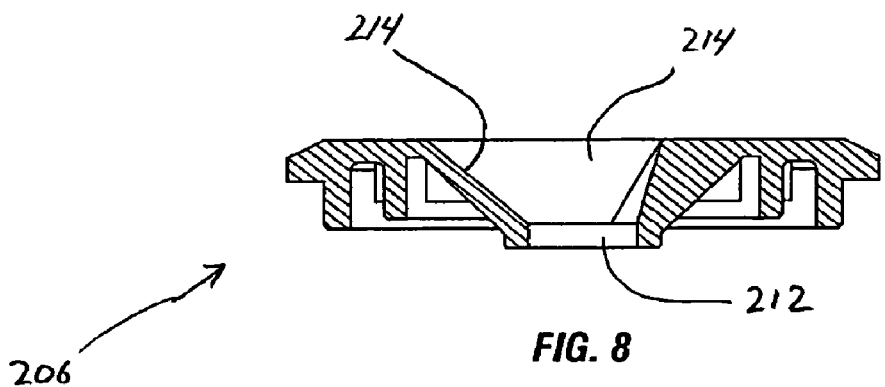
FIGS. 8-9 are cross-sectional views of the cover of FIG. 7 respectively taken along lines 8-8 and 9-9 of FIG. 7.
Figure 9:
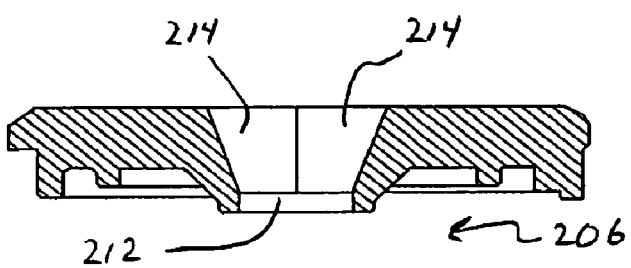
Figure 10:
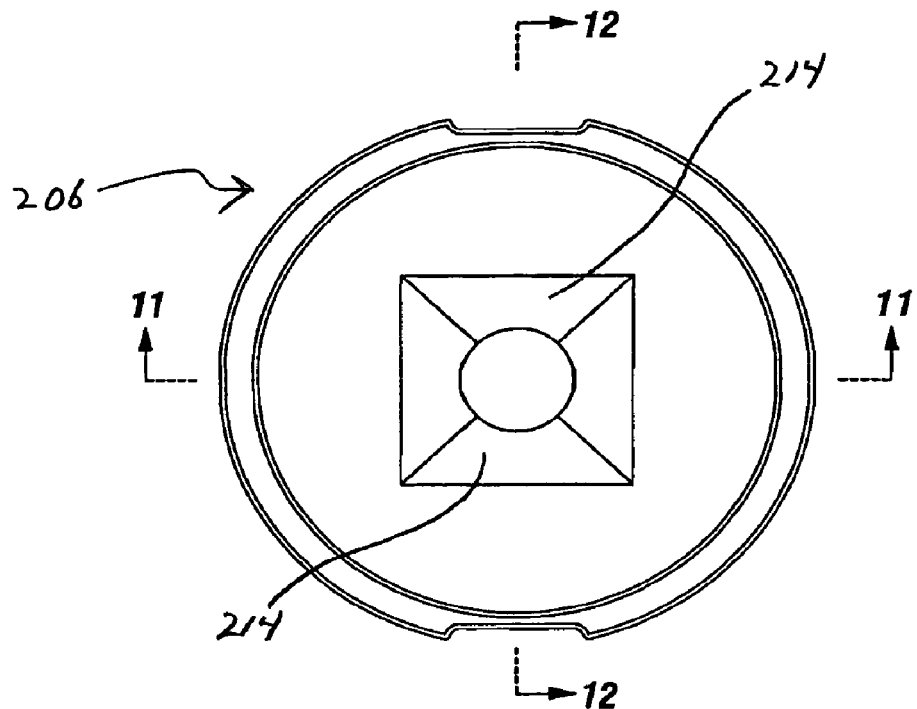
FIG. 10 is a top plan view of the another alternate embodiment of the cover of the seal assembly.
Figure 11:
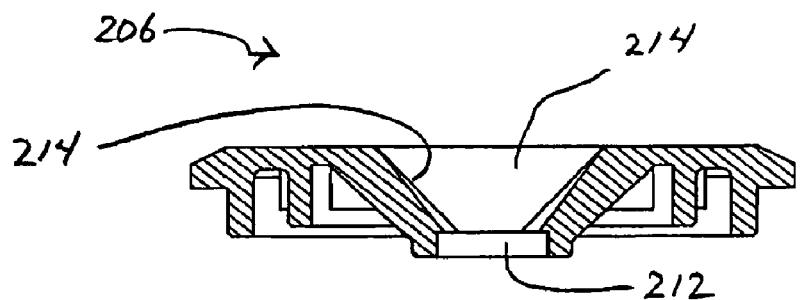
FIGS. 11-12 are cross-sectional views of the cover of FIG. 10 respectively taken along lines 11-11 and 12-12 of FIG. 10.
Figure 12:
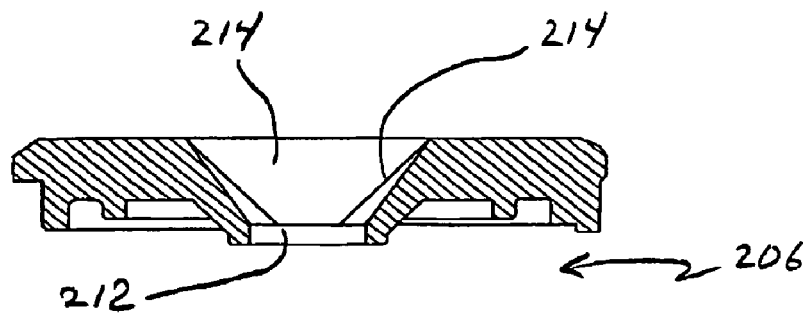
Figure 13:
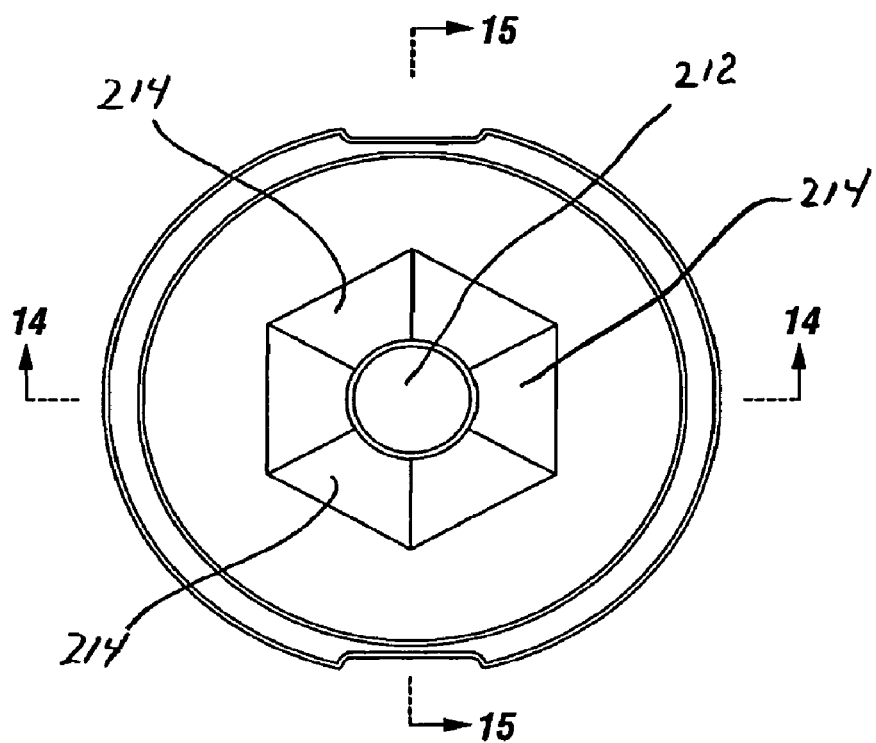
FIG. 13 is a top plan view of yet another alternate embodiment of the cover of the seal assembly.
Figure 14:
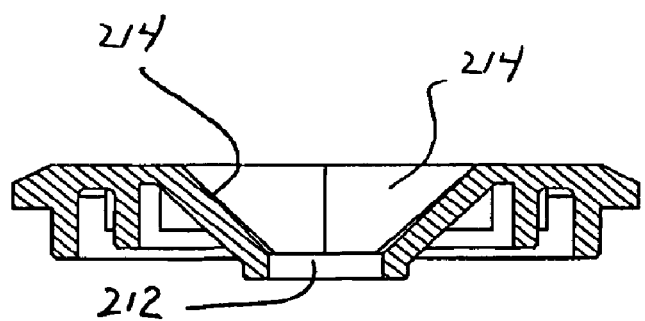
FIGS. 14-15 are cross-sectional views of the cover of FIG. 13 respectively taken along lines 14-14 and 15-15 of FIG. 13.
Figure 15:
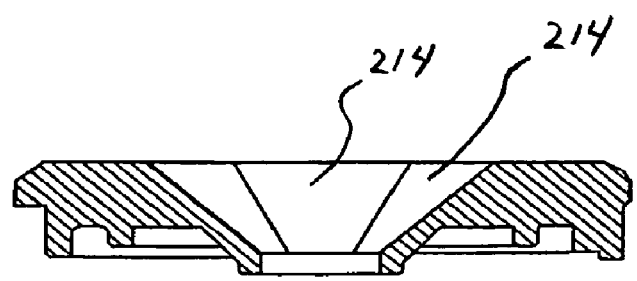

FIGS. 7-9 illustrate an alternate embodiment of cover 206 of the seal assembly of the present disclosure. In accordance with this embodiment, cover 206 includes a plurality, e.g., three, of intersecting entry surfaces 214 obliquely arranged relative to the seal axis and extending from proximal or entry opening 210 to distal or exit opening 212 of the cover 206. Entry surfaces 214 may be planar or arcuate and function to direct the instrument though distal opening 212 of cover 206. Entry surfaces 214 may be disposed in various angular relationships creating differing guidance pathways. FIGS. 10-12 illustrate cover 206 with four intersecting entry surfaces 214 and FIGS. 13-15 illustrate cover 206 with six intersecting entry surfaces 214. It is envisioned that any number of entry surfaces 214 may be incorporated into cover 206.

Figure 16:
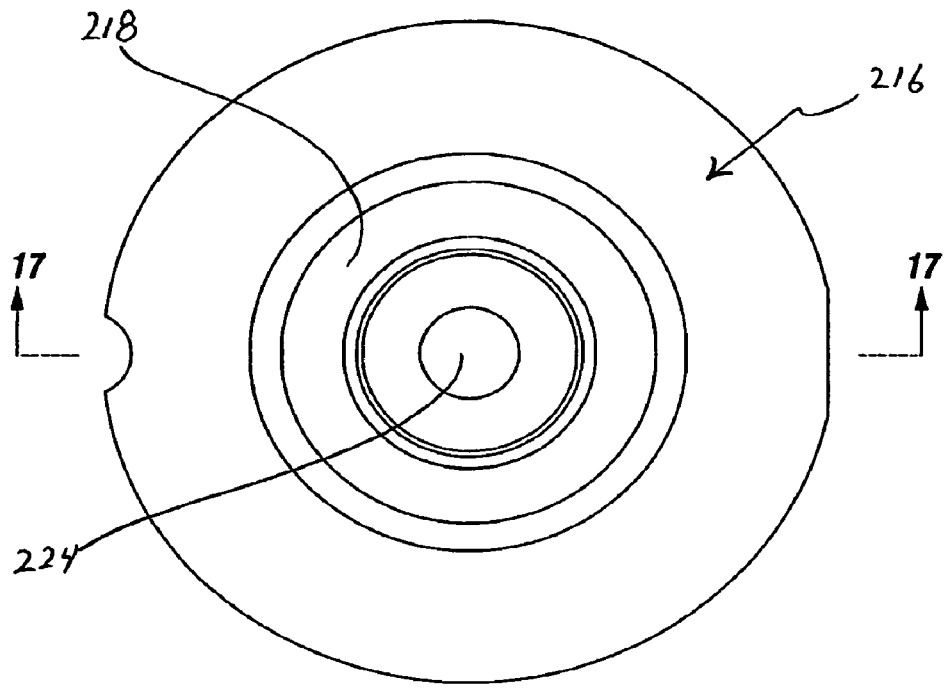
FIG. 16 is a top plan of the seal mount and resilient seal of the seal assembly.
Figure 17:
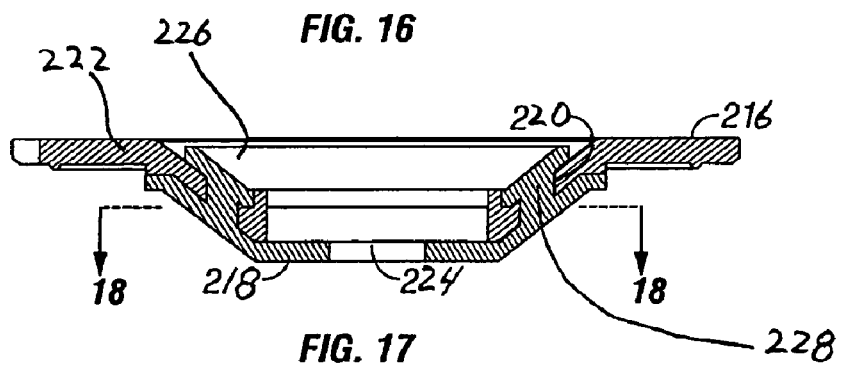
FIG. 17 is a cross-sectional view of the seal mount and resilient seal of the seal assembly taken along the lines 17-17 of FIG. 16.
Figure 18:
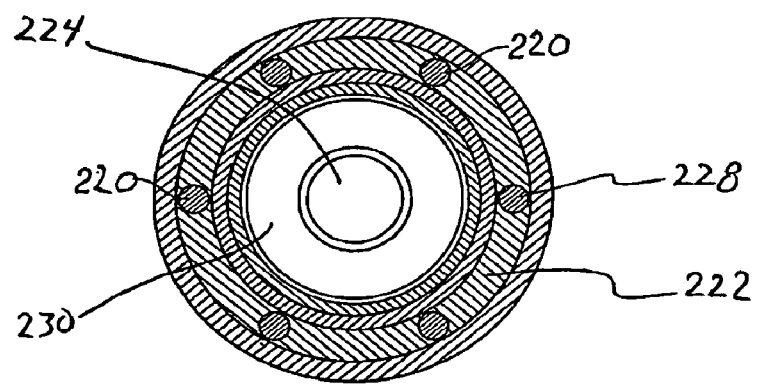
FIG. 18 is a cross-sectional view of the seal mount and resilient seal of the seal assembly taken along the lines 18-18 of FIG. 17.
Figure 19:
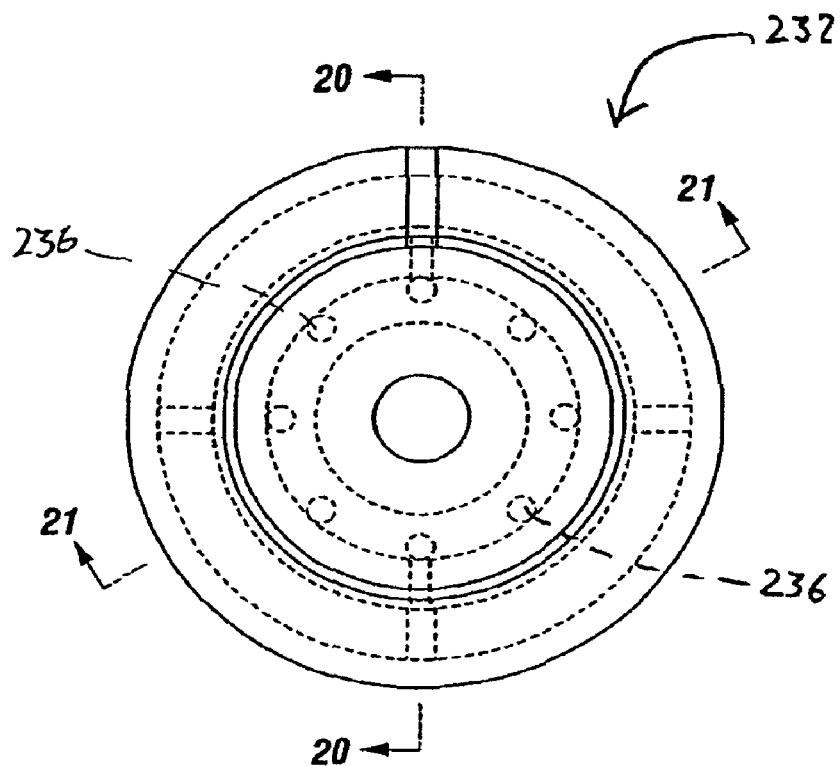
FIG. 19 is a top plan view of an alternate molded seal mount for use with the seal assembly.
Figure 20:
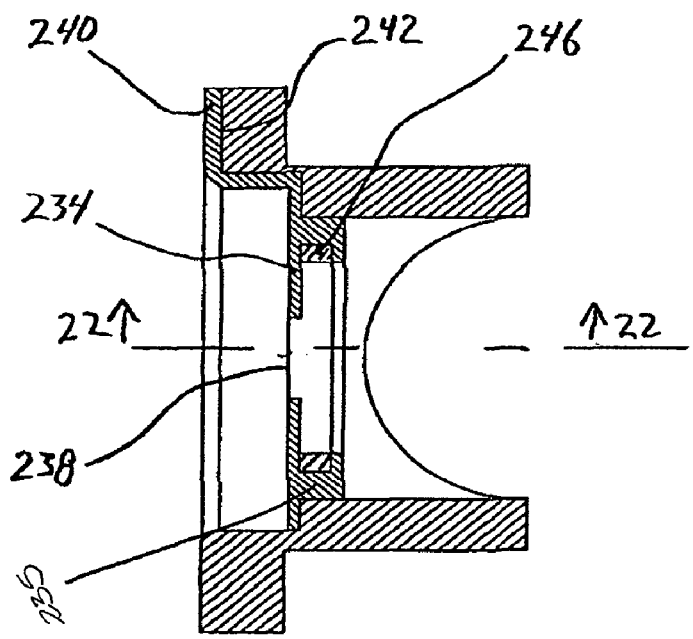
FIGS. 20-21 are cross-sectional view of the molded seal mount of FIG. 19 taken along the lines 20-20 and 21-21, respectively, of FIG. 19.
Figure 21:
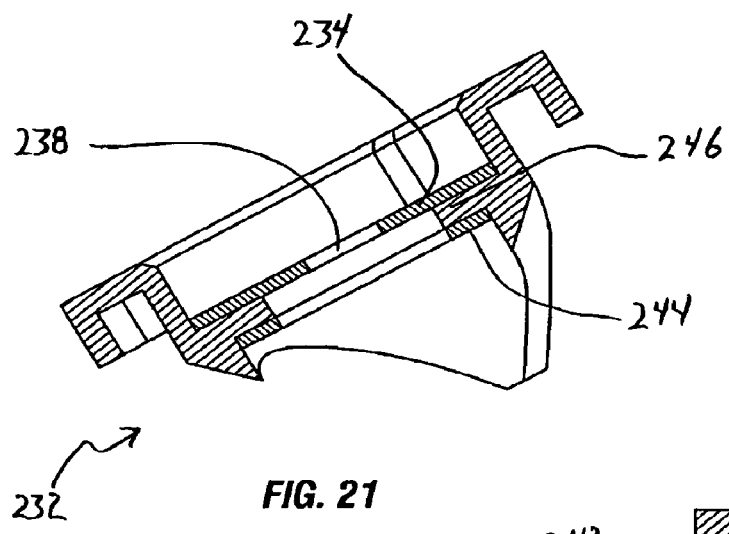
Figure 22:
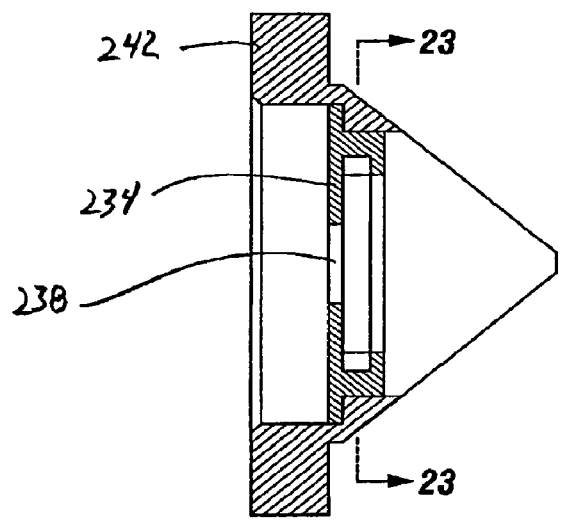
FIG. 22 is a cross-sectional view of the molded seal mount of FIG. 19 taken along the lines 22-22 of FIG. 20.
Figure 23:
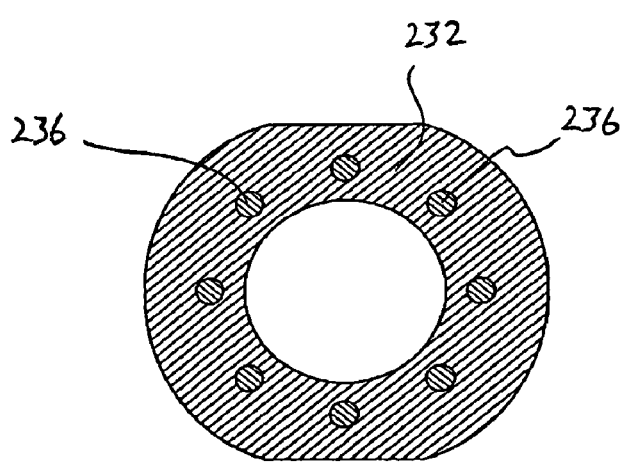
FIG. 23 is a cross-sectional view of the molded seal mount of FIG. 19 taken along the lines 23-23 of FIG. 22.

Referring now to FIGS. 16-18, seal 204 includes annular seal mount 216 and resilient seal 218 connected to the mount 216. Seal mount 216 may be formed of a relatively rigid material such as a suitable polymeric material or alternatively may be fabricated from a resilient material. Seal mount 216 incorporates a plurality of apertures 220 extending through wall 222 of the seal mount 216. Resilient seal 218 defines aperture 224 and is arranged to form a substantial seal about an instrument inserted therethrough. In a preferred embodiment, resilient seal 218 is adapted to form a seal about an instrument having a diameter ranging from about 3 mm to about 7 mm, preferably about 5 mm. In this regard, aperture 224 of seal 218 defines a diameter ranging from about 2 mm to about 3 mm. Seal 218 may be formed of any suitable elastomeric material. Preferably, seal 218 is integrally formed with seal mount 216 such that the elastomeric material communicates through apertures 220 to form the integrally coupled unit depicted in FIGS. 17-18. Seal mount 216 and seal 218 may be co-molded as is known in the art. In one preferred embodiment, seal 218 is molded with seal mount 216 to provide annular entry seal portion 226, anchoring segments or spokes 228 extending through apertures 220 of seal mount 216 and planar inner seal portion 230. Annular entry seal portion 226 defines a general frusto-conical configuration and provides an engagement area which may support cover 206 and may form a fluid-tight seal with the cover 200. Inner seal portion 230 defines aperture 224.

Seal 218 may be the fabric seal disclosed in commonly assigned U.S. Pat. No. 6,702,787 to Racenet, the entire contents of which are incorporated herein by reference. The seal disclosed in the Racenet '787 patent may be a flat septum seal having a first layer of resilient material and at least one fabric layer juxtaposed relative to the first layer. The fabric layer may include a SPANDEX material containing 20% LYCRA from Milliken. Other arrangements for seal 218 are also envisioned. Seal 218 may be flat, hemispherical or have any other shape as desired. Desirably, seal mount 216 has a shape corresponding to the shape of seal 218.

Referring now to FIGS. 19-23, an alternate embodiment of seal assembly 200 will be discussed. In accordance with this embodiment, an alternate seal mount 232 is utilized. Seal mount 232 is similar to seal support 208 discussed in connection with the embodiment of FIG. 1, e.g., assisting in maintaining zero closure valve 130 within cannula housing 108. However, seal mount 232 also has resilient seal 234 molded thereto to form an integrally coupled unit. Specifically, seal mount 232 includes a plurality of circumferentially disposed apertures 236 which permit flow of the elastomeric material during the molding process to secure resilient seal 234 to the seal mount 232 upon curing, i.e., by providing spokes 235 of resilient seal 234 extending through the apertures 236. Resilient seal 234 includes seal aperture 238 adapted to form a seal about an instrument inserted therethrough. Resilient seal 234 also has proximal gasket 240 extending contiguously, therefrom which resides on annular shelf 242 of seal mount 232, and distal gasket 244 extending from spokes 235 and in contact with internal annular wall 246 of seal mount 232. Proximal and distal gaskets 240,244 may assist in sealing the interior of seal assembly 200 and also securing resilient seal 234 to seal mount 232.

As best depicted in FIG. 1, seal housing 202 is adapted to be at least partially received within cannula housing 108 preferably with the wall 250 of cover 206 received within proximal collar 128 of cannula housing 108. Seal housing 202 may be dimensioned to be releasably mounted to cannula housing 108. In this regard, it is appreciated that seal housing 202 and cannula housing 108 may incorporate means for facilitating the releasable connection of seal assembly 200 to cannula assembly 100 including, e.g., an interference fit, bayonet coupling, screw arrangement, etc. . . . on corresponding structure of the seal housing 202 and cannula housing 108. Alternatively, seal housing 202 may be permanently secured to cannula housing 108 if desired.

Referring now to FIGS. 24-27, the adapter seal assembly 300 of the seal system will be discussed. Adapter seal assembly 300 provides greater flexibility to the surgeon by enabling the sealed introduction of instruments having a smaller diameter than that afforded by the aforedescribed seal assembly 200. Adapter seal assembly 300 includes adapter body 302, tether 304 and manual tab 306. Adapter body 302 is substantially circular in configuration and defines a central adapter axis "e". Adapter body 302 incorporates central seal section 308, transverse wall 310 extending from the central seal section 308 and peripheral wall 312 disposed outwardly of the transverse wall 310. Central seal section 308 includes tapered lead-in port 314 and septum seal 316. Tapered lead-in port 314 receives the instrument during insertion within adapter body 302. It is also envisioned that port 314 may be cylindrical and devoid of a taper. Septum seal 316 defines seal aperture 318 which is adapted to permit passage of the instrument whereby portions of the septum seal 316 defining the seal aperture 318 engage the outer surface of the instrument in substantial sealed relation therewith. Seal aperture 318 is preferably dimensioned to form a seal about an instrument with a relatively small diameter, e.g. 2-3 mm. Peripheral wall 312 defines a radially inwardly depending flange 320.

Figure 27:
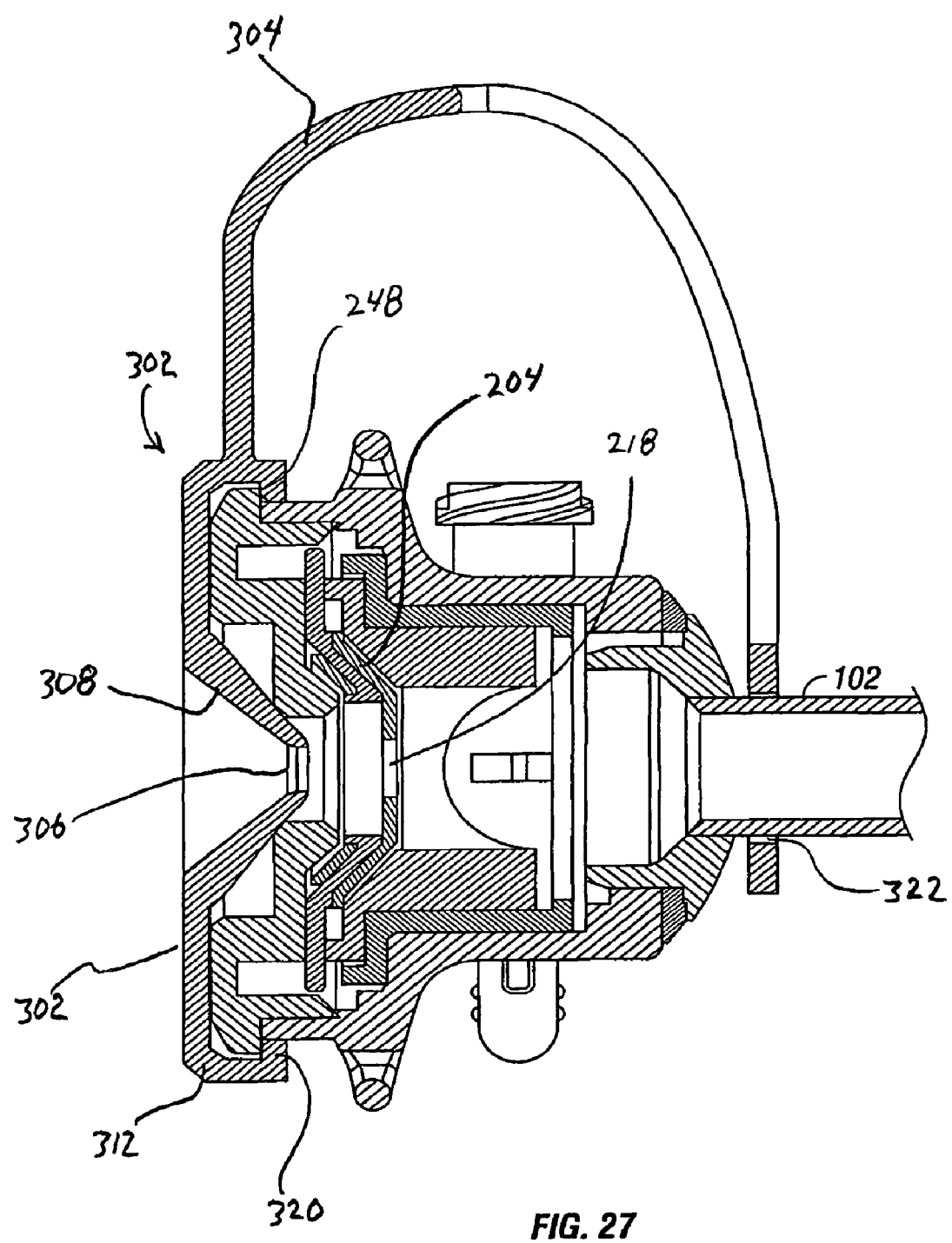
FIG. 27 is a side cross sectional view of the adapter seal assembly mounted to the seal assembly.

Tether 304 extends from one side of adapter body 302. Tether 304 has peripheral sleeve hole 322 which is adapted to be positioned over the outer surface of the sleeve 102 of cannula 100 as shown in FIG. 27. Tether 304 incorporates locking tab 324 and corresponding locking aperture 326. Locking tab 324 incorporates an arrow shaped locking head 328 which defines a dimension greater than a corresponding dimension of locking aperture 326. Locking head 328 and/or portions of tether 304 defining locking aperture 326 are sufficiently flexible to permit passage of the oversized locking head 328 through the locking aperture 326. Once cleared, locking head 328 and/or locking aperture 326 assume their normal condition with the locking head 328 secured relative to the locking aperture 328 thereby fixing tether 304 to the sheath or cannula. Other means for securing tether 304 to the cannula 100 are also envisioned by one skilled in the art including loop and hook arrangements, adhesives, strap means etc.

Figure 24:
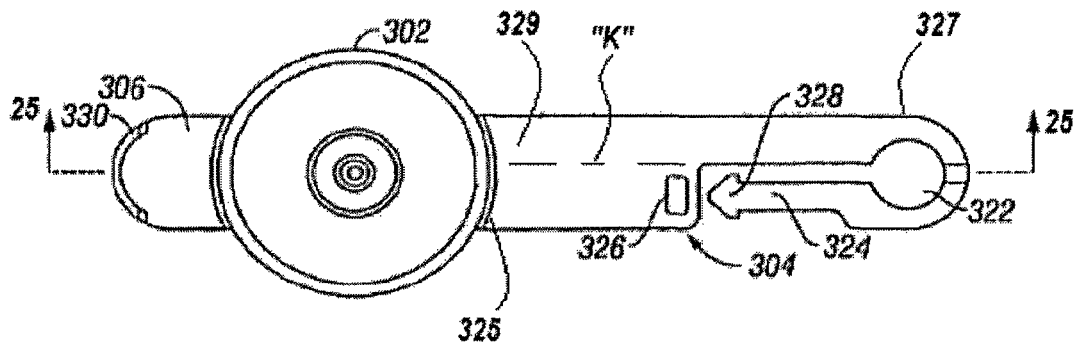
FIG. 24 is a top plan view of an adapter seal assembly of the seal system of FIG. 1.
Figure 25:
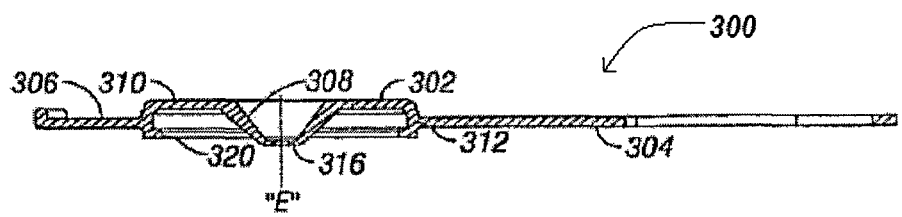
FIG. 25 is a side cross-sectional view of the adapter seal assembly.
Figure 26:
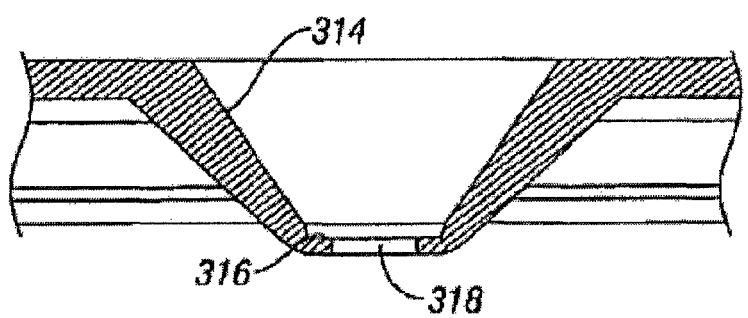
FIG. 26 is an enlarged isolated view illustrating the entry port and seal of the adapter seal assembly.

With continued reference to FIGS. 24-26, manual tab 306 extends from the other side of adapter body 302 opposed from tether 304. Manual tab 306 is adapted for engagement by the surgeon and incorporates a raised ridge 330 which facilitates gripping engagement by the surgeon.

With reference to FIG. 27, peripheral wall 312 of adapter body 302 is resilient and may stretch over cover 206 of seal assembly 200 to form a friction fit. It is also envisioned that radially inwardly extending flange 320 of adapter body 302 may be positioned over cover 206 to be positioned over ledge 248 of cover 206 of seal assembly 200 to positively fix the adapter body 302 to the seal housing 204. Adapter 300 is firmly mounted on the cannula housing 108 by pressing downward on adapter body 302 thus forming a seal between the cannula housing 108, seal housing 202 and adapter body 302.

Adapter seal assembly 300 is fabricated from an elastomeric material, e.g., santoprene or natural rubber, to provide a desired degree of resilience and flexibility thereto. This resilience and flexibility is desirable to permit efficient interaction between adapter seal assembly 300 and seal assembly 200, and to facilitate sealing engagement with an instrument passed through the seal aperture 218.

In use, a surgeon places cannula assembly 100 through a body wall in a conventional manner such that a port of entry for surgical instrumentation is established. The surgeon may utilize instrumentation sized to cooperate with the cannula assembly 100, and particularly the seal assembly 200 of the selected cannula assembly, without loss of pneumoperitoneum gas. If not already secured, seal assembly 200 may be secured to cannula assembly 100. Thereafter, the surgeon introduces an instrument, e.g., 5 mm instrument through seal assembly 200 while seal 204 forms a seal about the instrument. If the surgeon desires to use an instrument of diameter which is smaller than seal assembly 200 is designed to accommodate, adapter body 302 is positioned over seal housing 202 as depicted in FIG. 27 and secured to outer surface of the seal housing 202. The surgeon proceeds with the surgical procedure by inserting surgical instrument(s) of smaller diameter, e.g., 2 mm to 3 mm through seal 316. Adapter seal 316 thus sealingly engages the surgical instrument, thereby providing a gas seal therebetween.

Figure 28:
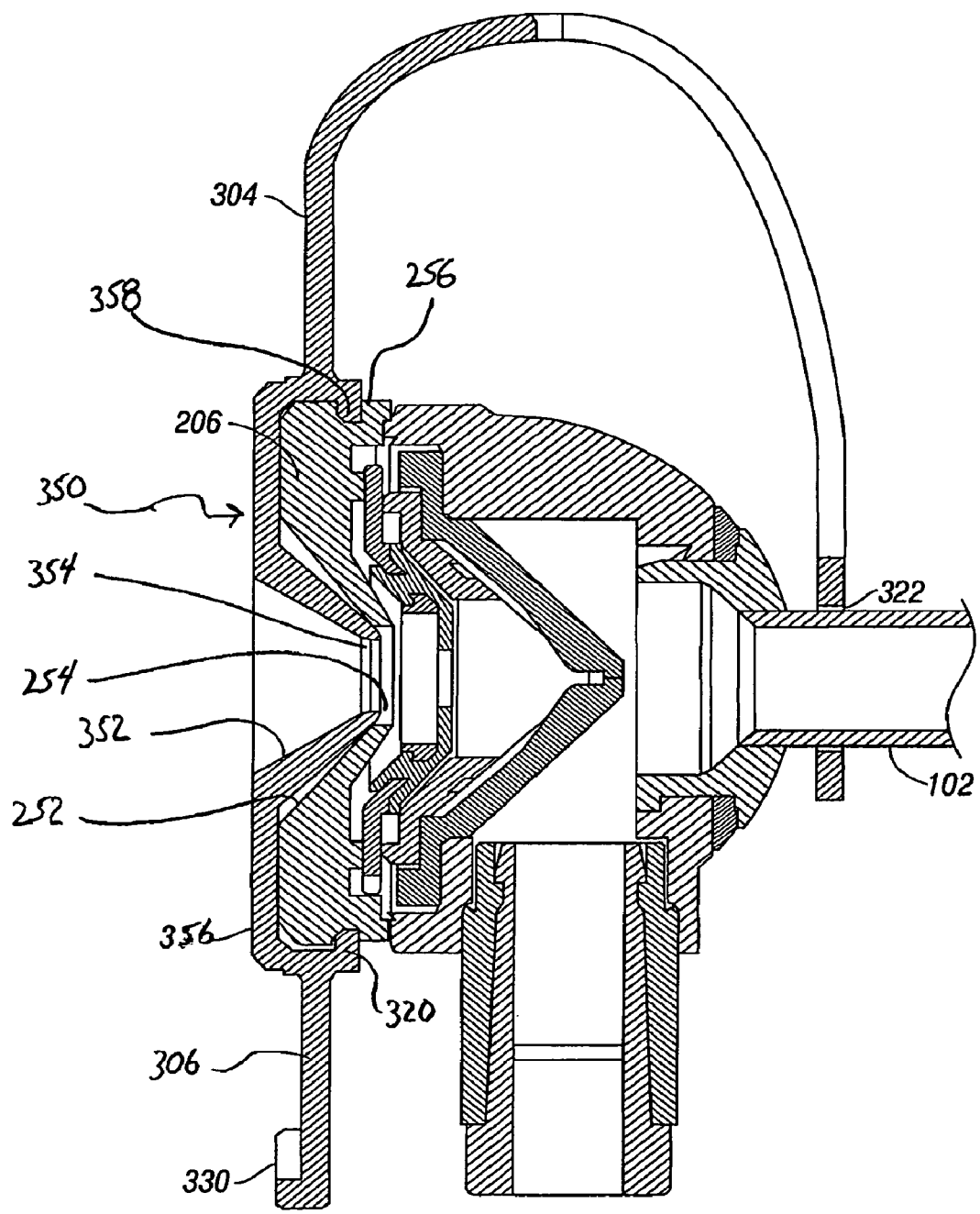
FIG. 28 is a side cross-sectional view of an alternate embodiment of the adapter seal assembly.

FIG. 28 illustrates an alternate embodiment of the seal system of the present disclosure. In accordance with this embodiment, seal cover 250 includes tapered wall 252 defining aperture 254. Adapter 350 includes correspondingly dimensioned tapered wall 352 which defines aperture 354. Tapered wall 252 of seal cover 250 supports tapered wall 352 of adapter 350 during introduction and manipulation of the instrument. In addition, aperture 354 of adapter 350 defines a diameter which is greater than the diameter of seal aperture 218 of seal 204 of seal assembly 200. Accordingly, when instruments of relatively small diameters are needed, seal assembly 200 is mounted to cannula assembly 100 and the small diameter instrument is passed through seal 204 of the seal assembly 200. When a relatively larger diameter instrument is required, seal assembly 200 may be removed from cannula assembly 100. Adapter assembly 350 may be then directly mounted to, or about, cannula housing 108 of cannula assembly 100 through, e.g., stretching adapter body 356 over the outer circumference of cannula housing 108. Adapter body 356 may include an internally directed rib 358 which is received in a correspondingly dimensioned annular groove 256 in seal cover 250. The larger diameter instrument is then introduced within adapter assembly 350 whereby portions defining aperture 354 sealingly engages the instrument. As an alternative, it is also envisioned that seal assembly 200 may remain mounted to cannula assembly 100 with adapter assembly 350 mounted to seal assembly 200. The large diameter instrument is then passed through seal aperture 354 of adapter assembly and seal aperture 218 of seal assembly 200.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical access system for passage of a surgical object, which comprises:
   an access assembly including:
      a housing; and
      an elongated access member extending from the housing, the access member dimensioned for passage through body tissue; and
   a surgical seal assembly including:
      a seal mount defining a seal axis and being at least partially positionable within the housing of the access assembly, the seal mount having a resilient seal member molded thereto, the seal member being integrally formed and defining inner seal portions adapted to form a substantial seal about a surgical object, the seal member including a plurality of resilient anchoring segments with adjacent anchoring segments being radially spaced apart with respect to each other, the seal mount including a plurality of peripherally disposed apertures whereby the resilient anchoring segments of the seal member are received within respective apertures to facilitate securing of the seal member to the seal mount.

2. The access system according to claim 1 wherein the seal mount is a generally annular seal mount and wherein the apertures are spaced adjacent peripheral areas of the seal mount.

3. The access system according to claim 1 wherein the seal mount and the seal member are integrally formed.

4. The access system according to claim 1 wherein the seal member includes an entry seal segment, the entry seal segment dimensioned to facilitate passage of the surgical object generally toward the inner portions of the seal member.

5. The access system according to claim 4 wherein the entry seal segment defines a general frusto-conical configuration.

6. The access system according to claim 5 wherein the seal mount includes a generally centrally located frusto-conical segment and an annular segment, the annular segment having the apertures for reception of the anchoring segments.

7. The access system according to claim 6 wherein the anchoring segments of the seal member are dimensioned to extend from the entry seal segment and through the apertures of the seal mount.

8. The access system according to claim 7 wherein the annular segment is in general orthogonal relation to the seal axis.

9. The access system according to claim 5 wherein the seal member includes an inner seal segment, the inner seal segment having the inner seal portions.

10. The access system according to claim 9 wherein the inner seal segment is substantially planar.

11. The access system according to claim 10 wherein the inner seal portions are arranged to define an aperture.

12. The access system according to claim 1 including a cover mountable to the seal mount.

13. The access system according to claim 1 wherein the housing of the access assembly includes a valve, the valve adapted to close in the absence of the surgical object.

14. The access system according to claim 1, wherein the anchoring segments are elastomeric.

15. The access system according to claim 1, wherein each anchoring segment occludes a corresponding aperture.

16. The access system according to claim 1, wherein the anchoring segments extend longitudinally through the apertures.

17. The access system according to claim 1, wherein the entirety of the seal member is made of the same material.

18. A surgical access system for passage of a surgical object, which comprises:
   an access assembly including:
      a housing; and
      an elongated access member extending from the housing, the access member dimensioned for passage through body tissue; and
   a surgical seal assembly including:
      a seal mount defining a seal axis and being at least partially positionable within the housing of the access assembly, the seal mount including a substantially annular outer mount segment having a plurality of apertures extending therethrough and an inner mount segment depending radially inwardly from the annular mount segment; and
      an integrally formed seal member molded onto the seal mount, the seal member including:
         an entry seal segment in juxtaposed relation to the inner mount segment of the seal mount;
         a plurality of resilient anchoring segments connected to the entry seal segment and dimensioned for passage through the apertures of the seal mount to facilitate securing of the seal member to the seal mount, adjacent anchoring segments radially spaced apart with respect to each other; and
         an inner seal segment connected to the anchoring segments, the inner seal segment having inner seal portions dimensioned and adapted to form a substantial seal about a surgical object.

19. The access system according to claim 18, wherein the anchoring segments are elastomeric.

20. The access system according to claim 18, wherein each anchoring segment occludes a corresponding aperture.

21. The access system according to claim 18, wherein the anchoring segments extend longitudinally through the apertures.

22. The access system according to claim 18, wherein the entirety of the seal member is made of the same material.

* * * * *